US009790560B2

(12) United States Patent
Sun et al.

(10) Patent No.: US 9,790,560 B2
(45) Date of Patent: Oct. 17, 2017

(54) **PRIMERS FOR DETECTING SEROTYPES OF *SHIGELLA FLEXNERI* AND MULTIPLEX AMPLIFICATIONS USING THE SAME**

(75) Inventors: Qiangzheng Sun, Beijing (CN); Jianping Wang, Beijing (CN); Jianguo Xu, Beijing (CN)

(73) Assignee: National Institute for Communicable Disease Control and Provention, China CDC (CN)

( * ) Notice: Subject to any disclaimer, the term of this patent is extended or adjusted under 35 U.S.C. 154(b) by 888 days.

(21) Appl. No.: 14/241,833

(22) PCT Filed: Aug. 29, 2012

(86) PCT No.: PCT/CN2012/080691
§ 371 (c)(1),
(2), (4) Date: Jun. 23, 2014

(87) PCT Pub. No.: WO2013/029537
PCT Pub. Date: Mar. 7, 2013

(65) Prior Publication Data
US 2015/0057168 A1    Feb. 26, 2015

(30) Foreign Application Priority Data
Aug. 29, 2011    (CN) .......................... 2011 1 0250513

(51) Int. Cl.
C12Q 1/68        (2006.01)
G01N 33/569      (2006.01)
C07H 21/02       (2006.01)

(52) U.S. Cl.
CPC ....... *C12Q 1/689* (2013.01); *G01N 33/56916* (2013.01); *C12Q 2600/112* (2013.01); *C12Q 2600/16* (2013.01)

(58) Field of Classification Search
CPC .............. C12Q 1/689; C12Q 2600/112; C12Q 2600/16; G01N 33/56916
See application file for complete search history.

(56) References Cited

U.S. PATENT DOCUMENTS 7,888,488 B2    2/2011 Portugal et al.

FOREIGN PATENT DOCUMENTS

CN    101429545 A      5/2009
CN    101532057 A  *   9/2009
(Continued)

OTHER PUBLICATIONS

Adams, M. M., et al., "Type IV O antigen modification genes in the genome of *Shigella flexneri* NCTC 8296," *Microbiology 147*:851-60, Society for General Microbiology, Great Britain (2001).
(Continued)

*Primary Examiner* — Teresa Strezelecka
(74) *Attorney, Agent, or Firm* — Dilworth IP LLC

(57) ABSTRACT

The present inventions relates to primers for identifying *Shigella flexneri* serotypes comprising the sequences of SEQ ID Nos. 1 and 2, SEQ ID Nos. 3 and 4, SEQ ID Nos. 5 and 6, SEQ ID Nos. 7 and 8, SEQ ID Nos. 9 and 10, SEQ ID Nos. 11 and 12, SEQ ID Nos. 13 and 14, SEQ ID Nos. 15 and 16. These primers are specific and have a common annealing temperature. The present invention further relates to a multiplex amplification-based identification method using the primers. The present invention further relates to the use of the primers for identifying *Shigella flexneri* serotypes for the preparation of identification agents. The present invention further relates to a kit for identifying *Shigella flexneri* comprising the above primers.

12 Claims, 2 Drawing Sheets

(56) References Cited

FOREIGN PATENT DOCUMENTS

Figure 1:
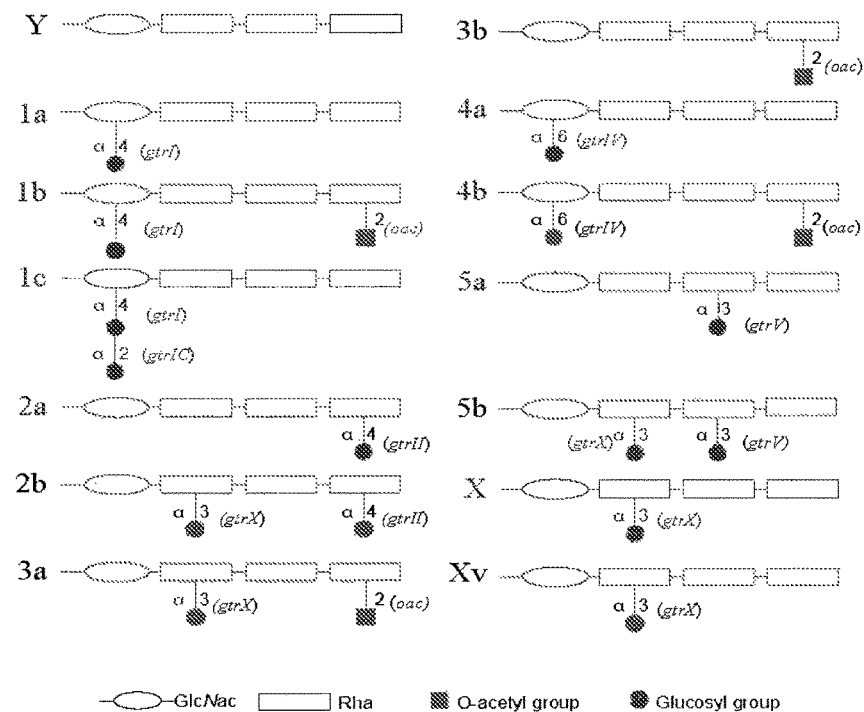

| CN | 101575637 A | 11/2009 |
|---|---|---|
| CN | 102329861 A | 1/2012 |

OTHER PUBLICATIONS

Adhikari, P., et al., "Serotype 1a O-antigen modification: molecular characterization of the genes involved and their novel organization in the *Shigella flexneri* chromosome," *J Bacteriol 181*:4711-8, American Society for Microbiology (1999).
Allison, G. E. and Verma, N.K., "Serotype-converting bacteriophages and O-antigen modification in *Shigella flexneri,*" *Trends. Microbiol. 8*:17-23, Elsevier Trends Journals, England (2000).
Cheah, K. C., et al., "Molecular cloning and genetic analysis of the rfb region from *Shigella flexneri* type 6 in *Escherichia coli* K-12," *FEMS Microbiol Lett 67*(2):213-8, Elsevier/North Holland on behalf of the Federation of European Microbiological Societies, England (1991).
Clark, C. A., et al., "The oac gene encoding a lipopolysaccharide O-antigen acetylase maps adjacent to the integrase-encoding gene on the genome of *Shigella flexneri* bacteriophage Sf6," *Gene 107*:43-52, Elsevier/North-Holland, Netherlands (1991).
Foster, R. A., et al., "Structural elucidation of the O-antigen of the *Shigella flexneri* provisional serotype 88-893: structural and serological similarities with *S. flexneri* provisional serotype Y394 (1c)," *Carbohydr Res 346*:872-6, Elsevier, Netherlands (2011).
Guan, S., et al., "Functional analysis of the O antigen glucosylation gene cluster of *Shigella flexneri* bacteriophage SfX," *Microbiology 145*: 1263-73, Society for General Microbiology, Great Britain (1999).
Huan, P. T., et al., "Molecular characterization of the genes involved in O-antigen modification, attachment, integration and excision in *Shigella flexneri* bacteriophage SfV," *Gene 195*:217-27, Elsevier Science B.V., Netherlands (1997).
Kotloff, K. L., et al., "Global burden of *Shigella* infections: implications for vaccine development and implementation of control strategies," *Bull World Health Organ 77*(8):651-66, World Health Organization,Switzerland (1999).
Li, Y., et al., "Molecular detection of all 34 distinct O-antigen forms of *Shigella,*" *J Med Microbiol 58*:69-81, Society for General Microbiology, Great Britain (2009).
Mavris, M., et al., "Mechanism of bacteriophage SfII-mediated serotype conversion in *Shigella flexneri,*" *Mol Microbiol 26*(5):939-950, Blackwell Science Ltd, England (1997).
Pryamukhina, N. S., and Khomenko, K. A., "Suggestion to supplement *Shigella flexneri* classification scheme with the subserovar *Shigella flexneri* 4c: phenotypic characteristics of strains," *J Clin Microbiol 26*(6):1147-9, American Society for Microbiology, United States (1988).
Simmons, D. A. R., and Romanowska, E., "Structure and biology of *Shigella flexneri* O antigens," *J. Med. Microbiol. 23*(4):289-302, The Pathological Society of Great Britain and Ireland, England (1987).
Stagg, R. M., et al., "Identification of newly recognized serotype 1c as the most prevalent *Shigella flexneri* serotype in northern rural Vietnam," *Epidemiol Infect 136*(8):1134-40, Cambridge University Press, England (2008).
Stagg, R. M., et al., "A novel glucosyltransferase involved in O-antigen modification of *Shigella flexneri* serotype 1c," *J. Bacteriol. 191*(21):6612-7, American Society for Microbiology, United States (2009).
Talukder, K. A., et al., "Phenotypic and genotypic characterization of provisional serotype *Shigella flexneri* 1c and clonal relationships with 1a and 1b strains isolated in Bangladesh," *J Clin Microbiol 41*(1):110-7, American Society for Microbiology, United States (2003).
Verma, N. K., et al., "Molecular characterization of the O-acetyl transferase gene of converting bacteriophage Sf6 that adds group antigen 6 to *Shigella flexneri,*" *Mol. Microbiol. 5*:71-5, Blackwell Scientific Publications, England (1991).
Von Seidlein, L., et al., "A multicentre study of *Shigella* diarrhoea in six Asian countries: disease burden, clinical manifestations, and microbiology," *PLoS Med 3*:e353, Public Library of Science, United States (2006).
Yao, Z. and Valvano, M.A., "Genetic analysis of the O-specific lipopolysaccharide biosynthesis region (rfb) of *Escherichia coli* K-12 W3110: identification of genes that confer group 6 specificity to *Shigella flexneri* serotypes Y and 4a," *J Bacteriol. 176*(13):4133-4143, American Society for Microbiology, United States (1994).
Ye, C., et al., "Emergence of a new multidrug-resistant serotype X variant in an epidemic clone of *Shigella flexneri.*" *J. Clin. Microbiol. 48*(2):419-26, American Society for Microbiology, United States (2010).
International Search Report for International Application No. PCT/CN2012/080691, State Intellectual Property Office of the People's Republic of China, China.
English language abstract of Chinese Patent Application No. CN 101429545 A, European Patent Office, espacenet database—Worldwide (2009).
English language abstract of Chinese Patent Application No. CN 101575637 A, European Patent Office, espacenet database—Worldwide (2009).
English language abstract of Chinese Patent Application No. CN 102329861 A, European Patent Office, espacenet database—Worldwide (2012).
English translation of Office Action in Chinese Application No. CN 201110250513.4, dated Sep. 20, 2012.

\* cited by examiner

SEQUENCE LISTING

<160> NUMBER OF SEQ ID NOS: 27

<210> SEQ ID NO 1
<211> LENGTH: 22
<212> TYPE: DNA
<213> ORGANISM: Artificial Sequence
<220> FEATURE:
<223> OTHER INFORMATION: Primer

<400> SEQUENCE: 1
ctgttaggtg atgatggctt ag          22

```
<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2
attgaacgcc tccttgctat gc                                              22

<210> SEQ ID NO 3
<211> LENGTH: 24
<212> TYPE: DNA
<213> ORGANISM: Artificial Sequence
<220> FEATURE:
<223> OTHER INFORMATION: Primer

<400> SEQUENCE: 3
atttattgtt attggggtg gttg                                             24

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
atttgttctt tatttgctgg tt                                              22

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
ctgttcggct ttgaaagtgc tg                                              22

<210> SEQ ID NO 6
<211> LENGTH: 25
<212> TYPE: DNA
<213> ORGANISM: Artificial Sequence
<220> FEATURE:
<223> OTHER INFORMATION: Primer

<400> SEQUENCE: 6
cgtaggcgta catagcaagc aaaga                                           25

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
atgttcctcc ttcttccttt                                                 20

<210> SEQ ID NO 8
<211> LENGTH: 20
<212> TYPE: DNA
<213> ORGANISM: Artificial Sequence
<220> FEATURE:
<223> OTHER INFORMATION: Primer
```

```
<400> SEQUENCE: 8
tcctgatgct accttatcca                                           20

<210> SEQ ID NO 9
<211> LENGTH: 24
<212> TYPE: DNA
<213> ORGANISM: Artificial Sequence
<220> FEATURE:
<223> OTHER INFORMATION: Primer

<400> SEQUENCE: 9
aatacgattc tcctggtgct aaac                                      24

<210> SEQ ID NO 10
<211> LENGTH: 24
<212> TYPE: DNA
<213> ORGANISM: Artificial Sequence
<220> FEATURE:
<223> OTHER INFORMATION: Primer

<400> SEQUENCE: 10
tagggcattg cttgtatctt tcat                                      24

<210> SEQ ID NO 11
<211> LENGTH: 24
<212> TYPE: DNA
<213> ORGANISM: Artificial Sequence
<220> FEATURE:
<223> OTHER INFORMATION: Primer

<400> SEQUENCE: 11
aatgctggat gggataatca cctt                                      24

<210> SEQ ID NO 12
<211> LENGTH: 24
<212> TYPE: DNA
<213> ORGANISM: Artificial Sequence
<220> FEATURE:
<223> OTHER INFORMATION: Primer

<400> SEQUENCE: 12
gagacggctt ctccatgttt tgct                                      24

<210> SEQ ID NO 13
<211> LENGTH: 19
<212> TYPE: DNA
<213> ORGANISM: Artificial Sequence
<220> FEATURE:
<223> OTHER INFORMATION: Primer

<400> SEQUENCE: 13
cacttgttgg gtatgctgg                                            19

<210> SEQ ID NO 14
<211> LENGTH: 19
<212> TYPE: DNA
<213> ORGANISM: Artificial Sequence
<220> FEATURE:
<223> OTHER INFORMATION: Primer

<400> SEQUENCE: 14
ccggcaaaca gattagaaa                                            19

<210> SEQ ID NO 15
```

```
<211> LENGTH: 22
<212> TYPE: DNA
<213> ORGANISM: Artificial Sequence
<220> FEATURE:
<223> OTHER INFORMATION: Primer

<400> SEQUENCE: 15
agggaatggc attagggatc gg                                              22

<210> SEQ ID NO 16
<211> LENGTH: 22
<212> TYPE: DNA
<213> ORGANISM: Artificial Sequence
<220> FEATURE:
<223> OTHER INFORMATION: Primer

<400> SEQUENCE: 16
gctgcaagtg gttttgttg ga                                               22

<210> SEQ ID NO 17
<211> LENGTH: 17
<212> TYPE: DNA
<213> ORGANISM: Artificial Sequence
<220> FEATURE:
<223> OTHER INFORMATION: Primer

<400> SEQUENCE: 17
ttaagagcga tcatttc                                                    17

<210> SEQ ID NO 18
<211> LENGTH: 17
<212> TYPE: DNA
<213> ORGANISM: Artificial Sequence
<220> FEATURE:
<223> OTHER INFORMATION: Primer

<400> SEQUENCE: 18
ccatccaagc ggacatt                                                    17

<210> SEQ ID NO 19
<211> LENGTH: 1122
<212> TYPE: DNA
<213> ORGANISM: Artificial Sequence
<220> FEATURE:
<223> OTHER INFORMATION: Probe

<400> SEQUENCE: 19
ctgttaggtg atgatggctt agtagcatta agattatcaa ctgcagtttt ctctattgct      60
atagtaatag cagcgatgtt aacgctacgt aaggcattcg ggtttacccc tgctttattt     120
tctattatac ttctatctct aataccatat ttttcataca cttatggttt tgtatcacat     180 ccttttctc ataattcaac aaacgctttc ggcttttat gcttgcttat atctgttttc      240
aacatacagt ataaaaatat atttatcact ctcctcttaa gttgacagc attattttcc      300 agcgtatccg atccgtggtt tacagctgca ttttttattc cactattaat atcttacttt     360
ttattctctg tatgggataa aaaattattt aagcatactg cattaatact atttgcatgt     420
ttaatctctc tttccaatgt attgcaaaat ctacttaaca tacctcccca ccaatttgaa     480
attgtatcac tcaatgatat gattttaaat gcaaatggt gcattctgtt aataggaaaa      540
agtcttaatt tattagttgt cgacaataac gcaacatctt acgcctcatt tgtcatttgg     600
ttcattgcca ttattacatc tgcgtggttt gttttatcgg acaataaaaa aaacacatac     660
cgtatttata ttgtgttatt ttcattatta tctatcgcag gtattgtctc atcattcata     720
```

```
ctgagctata aatcccctga ttatattagc atgcgtttct ttatgaatgt tacctgtttc      780
gcactgatat tgtgctgtat cggtacatca acaaaagcaa agatattatt ttatctaatc      840
gcatttttat tttcgatcag ttcaattaaa tcttacacaa ataatgcttc accattacac      900
gatcaggaga agattgttaa atcatacatt gattttttaa aaaaaaataa tctccattat      960
gggtacggct cttttgggga tttgtcaatg actgtaaatt ggttatctgg tggggacata     1020
cagataactc ctgttttctt taatgctgat tcggggaaaa ttaactttac tggcgtgaga     1080
caacagacac tggcttcttg catagcaag gaggcgttca at                         1122
```

<210> SEQ ID NO 20
<211> LENGTH: 1268
<212> TYPE: DNA
<213> ORGANISM: Artificial Sequence
<220> FEATURE:
<223> OTHER INFORMATION: Probe

<400> SEQUENCE: 20

```
atttattgtt attgggggtg gttgtacgat ggaacactta atattgatgg cgagtttaca       60
aataattttt atcaaacaat cacgcttggg cggtggtttc acactttttt gcgacattac      120
tttctccctg agcctttttc actttatata acaccattaa tagccttatc ttttatcatc      180
atttcagcat ttataatctg cagatcgcta aagctagaat cttatgaatt attgataggt      240
atgttagtat ttattacctt ccctcagatc tcctatcaat tagagtttct taaccaagct      300
gatactgtgg gaattgcttt tctactggca gcgatatcag caattatttt tcactcgcaa      360
aaaaatagga ttgtgatatt ttctggtata gtactgtcca ttctttcaat ggcaatctac      420
caaacattcg taacatatat tattgcattc gtcattgggt tgcagataaa ttcgataata      480
cgaaatgaga aaaatattcg tgaatctttt tatagttcat gtttatctct atccctcata      540
gctttatcta ccttaattta cctgctatta accaaagcta tcaagcatta ttttttcgctt     600 gaatcgaacg agtacatctc aaattatata caaaatgcaa gcgatattaa atggcttgtt      660
aaatcagcca tagataatat ataaacttc tataacaatc ctcccactgg tttaaaccta      720
tacaagtggt tactgattcc tttattaatt ctgatattta ccctaacata taaattaaaa      780
acaagatcaa tttatttgat ttcatcaatc attttcattt atatacttcc ggttatattt      840
atcgttgttg ttggctcagg ggcgccacct cgcctgtttg ttttaatgcc tatagtagca      900
gtaattttgt tttcttgctt aagcaatttt cgctctataa aatacctaaa ctgcatgttt      960 tttttatttta ttatatttaa tggcgtttca acatccaaaa atctattttt gaatgatact     1020
ctcgcaagac agaaagatat ctctttagct aaagaaatat catacacatc tcaaacaaaa     1080
ggcatttccc ttaacggaaa atatatatat atacatggtt caaacgactc aggaaatatg     1140
ctctccatga gcgcagacac ttttggaaaa tctttttttt ggtgggatgg tggcaactat     1200
tttaggatgg ttgcatttat gaattactat gaaatctgta attgcaaacc agcaaataaa     1260
gaacaaat                                                             1268
```

<210> SEQ ID NO 21
<211> LENGTH: 604
<212> TYPE: DNA
<213> ORGANISM: Artificial Sequence
<220> FEATURE:
<223> OTHER INFORMATION: Probe

<400> SEQUENCE: 21

| | |
|---|---|
| cgtaggcgta catagcaagc aaagaaacta cagtaatttt aacattactt acattccatg | 60 |
| acttctcata cattgccata gtggcaccaa aaaagaacgc cagtccacgc aaaggataca | 120 |
| gccataacgg aatagagaac attacatccc tgttttctga cacacttcca attaatgaaa | 180 |
| gagaaacaaa aaccaacagt ataactatga atgcttttcc gttctttagt agggcaactg | 240 |
| ctactcccgt tattatataa cacaggaact caagcggtag ggtccacaaa ctgccgttaa | 300 |
| ttccggcatg aattaaatgt gatgtaatgt cagcatctgg agcctgactc ataaaaatag | 360 |
| agcttatggt cttcctgaca atgtcatggc taaaatattc tgcgctgaag tcgttaagta | 420 |
| tccatccaaa taaaaatat gtcagtatag agcaagggac cagcgccggg aatattcttc | 480 |
| tcgctctttt agccatgaaa tcaataaagg aatcactcct gatagctgat tttgaaatca | 540 |
| gatatcctga tattgaaaag aatatgataa ctgcaatgcc gccagcactt tcaaagccga | 600 |
| acag | 604 |

<210> SEQ ID NO 22
<211> LENGTH: 378
<212> TYPE: DNA
<213> ORGANISM: Artificial Sequence
<220> FEATURE:
<223> OTHER INFORMATION: Probe

<400> SEQUENCE: 22

| | |
|---|---|
| atgttcctcc ttcttccttt tgattctgga gttcgaaccc aattaactga agattacttc | 60 |
| catgtcttca aggaaaataa gctaataata agtaagagtg ttttttttgaa tgaagttcaa | 120 |
| aaaataaaag actctgctct atcaactgtg aggattcctg ttgcatttat agccatgata | 180 |
| gcatcactga ttttatccg aaaaaaatat tctgttgcaa tctttacatt atctgctttt | 240 |
| agcatctctc agttttatat tagcttcatt ggcgaaggat atagagattt agacaagcat | 300 |
| cttttttgcaa tgaacttttc atttgaccta atgatattta tagtactatc aattatattg | 360 |
| gataaggtag catcagga | 378 |

<210> SEQ ID NO 23
<211> LENGTH: 905
<212> TYPE: DNA
<213> ORGANISM: Artificial Sequence
<220> FEATURE:
<223> OTHER INFORMATION: Probe

<400> SEQUENCE: 23

| | |
|---|---|
| aatacgattc tcctggtgct aaactttcaa atttttaac ttgctctttc cacccgtaat | 60 |
| ctgggagtgg ggtaagattg aaaaaatata acatgagat taacgatgtt gtatataata | 120 |
| tccatggtag gaatttaaag tccaactggg aaatatggtt taagaagtaa accaatacag | 180 |
| agtaccatat aattgttggt atgacagaat atcttccccc gccatgaatt aataatggcc | 240 |
| attgctcact tgtagaagaa agcattggtt ttgctagtga aaacgttaat gttagtattg | 300 |
| cgaaaactat tgccgagcgc atggggtaat tggaaacaat aaatgtaaaa atagtgatgg | 360 |
| aaagacaaat cattgtaatt gcaatgcaaa ttgatcatg attccataaa ggtggcaaaa | 420 |
| agtcaccatt agcccataaa cccagaaaaa cctttgttgt taatattttg caaagtgttg | 480 |
| cgaaattagc tccaagaacc atatcaactc tggtctcaga ggatgtcatg ataatagaaa | 540 |
| taaattgaat caaacaaata gcaatgaaaa cgtattcgtg agtggtgatt ttttttgtag | 600 |
| ataagcgttt ttgtataagt atatttatcc ctaccattgg agccatgaac actataaatg | 660 |
| ggccacttag tccacatatg attatcgcta tataatcgtg tgcttttttga taattatttg | 720 |

```
taggctttgg agctaacata acaagaagta aatatagtga taaataccaa tgatcattag    780
taacattggc gtgcacttct gatacttccg gcattgttat aataaacaaa gcagtaaata    840
ttcttggtgt tatgtttacg taactaaatc ttccagagag tatgaaagat acaagcaatg    900
cccta                                                               905

<210> SEQ ID NO 24
<211> LENGTH: 425
<212> TYPE: DNA
<213> ORGANISM: Artificial Sequence
<220> FEATURE:
<223> OTHER INFORMATION: Probe

<400> SEQUENCE: 24
aatgctggat gggataatca ccttttatcg tacacactat caactttagt aattacatta     60
tgtgttttca tttatattaa aggaaattgg caaatgaaag tgtttgccac ccttccaata    120
cttattgtcg cattttctat ggcaaaacct caactggcag attctgttcc tcaactgcca    180
acacttgcaa ccggaaacgg gtcaaggtat tttgtaaata ttcatattgc aattttttca    240
ttaatatgcg tttgtttgtt tcaatgcata aagaataaaa ccttaaaaat attctttaaa    300
atctatgttt cagtcatcct tattgcaatg ataaaattaa acttttttat aaccccctctt   360 cctgacatga actggtctca aggagcagaa ttaataaata aagcaaaaca tggagaagcc    420
gtctc                                                               425

<210> SEQ ID NO 25
<211> LENGTH: 783
<212> TYPE: DNA
<213> ORGANISM: Artificial Sequence
<220> FEATURE:
<223> OTHER INFORMATION: Probe

<400> SEQUENCE: 25
ccggcaaaca gattagaaac attaaaagca atgatttatt tacattacgt ttaaattctt     60
taaagtcttt gatgttactt aaccttggaa acactgccct cccgattgct gcaggtatta    120
ttcctaattt tagaataacc tccgctggtg cagaataaaa tgcaactta tctgccccca    180 taatatttga cactataaat cgatcaaaat acaccatgac cggacttatg atattactta    240
ctgtcatcca accgccaaag aaaaagagtc gtttaaaggt tttataacaa aaatgaaccc    300
ccgaaatttt aatatcattc ctgacataat aggcagagac taaaatcgaa ataactcttg    360
caaatattaa accagcaacc gctgccgaca atgtagcact ataaaaaaca aatatggccg    420
gaattcccgc gatgcaagag cttgatatag attttttgaat atttacaatg ccaaattttt    480
catccccctc aagaatggct gaccataatt gatttagaat aaataatgga atgcaaatag    540
ccaacagttt aaatgctagt tgtatatcac tatgttcaac accagaaatt tttagataat    600
taacaattcc atcagagaaa atcaataata aaaagcacc aaagcatgaa aatagcacca    660
aaaaagatgt acttgttgaa attaccttgg ttctttcatg atgattatca cgatgaattg    720
caatttctct aataacagag cgagtcaggc ctacatcaaa aattccagca tacccaacaa    780
gtg                                                                 783

<210> SEQ ID NO 26
<211> LENGTH: 518
<212> TYPE: DNA
<213> ORGANISM: Artificial Sequence
<220> FEATURE:
```

```
<223> OTHER INFORMATION: Probe

<400> SEQUENCE: 26
agggaatggc attagggatc ggactgccaa ttacctttgc atttatatgg aactttgcga      60
cagatcacaa taaaagaaa caagattacc tgcttgtttt aattatattg ctaatcattt      120
gtggtggcat taattttggt tttctaggtg gcgtatttac acatttatca aaaattcaat    180
ttacttggcg ttttattcca ttcctgctat ttagcatttt acttattctc catgcatcag    240
gaagaatcaa attaaaatat atcttgttaa ttttcacatc aacatgtttg atgacaagtg    300
cgattactgt acctaaaaaa agtagccaca acctcacaat tgatattgcc gccagtgcaa    360
attataaaga ttatgttcta tcaaatgcac cagagcttgg tgaccggatt aaagaattaa    420
aatgcgataa tgggctgtca tacgctttct cacgaaacct aggttcaaat gggttacctg    480
ttttcacatt tagtattcca acaaaaacca cttgcagc                             518

<210> SEQ ID NO 27
<211> LENGTH: 739
<212> TYPE: DNA
<213> ORGANISM: Artificial Sequence
<220> FEATURE:
<223> OTHER INFORMATION: Probe

<400> SEQUENCE: 27
ttaagagcga tcatttcaac ttcaacggta attctaacta tattgggctt gattggcggt      60
agtgtactat ttttgagtag caatgtaatt gttaaattat taaacattaa cgcgaatcat    120
gttgtagaat ctgtcaaagc aatatatatt atttcagcta ccatacccct atacttgtta    180
aaccaagtct ggttggggat ttttgagggg atggaaaagt tcagaaaagt aaatttaata    240
aaatcaatta caactctttt tgtggctgga ttaccagtga ttttctgttt ttttcatgga    300
ggattactaa gtgctatata tggtttagtt atggcaagag tcttatcact tatagtgacc    360
tttatattta gtcgaaaact aataatatca tctgggctgt ctgtaaaaat tgtaacagtt    420
aaaagattaa tcggctttgg aagctggata acagttagca atattattag ccctattatg    480
acatatatgg atcgttttat tctttcacac attgtggggg ctgataaagt ttcttttttat    540 actgctccgt ctgaaggtat acaacgctta acgatattac caagtgcgtt gtccagagct    600
atttttccaa gattaagttc agaattgcaa tcggtaaagc aaactaaaat attatcatat    660
tttataatgg ttattggtat acttccaatt gtaatgttga taattatttt atcagatttt    720
ataatgtccg cttggatgg                                                  739
```

US 9,790,560 B2

PRIMERS FOR DETECTING SEROTYPES OF *SHIGELLA FLEXNERI* AND MULTIPLEX AMPLIFICATIONS USING THE SAME

REFERENCE TO SEQUENCE LISTING SUBMITTED ELECTRONICALLY

The content of the electronically submitted sequence listing, file name: 3503_0010001_Sequence_Listing.txt; size: 13,842 bytes; and date of creation: Oct. 22, 2014, filed herewith, is incorporated herein by reference in its entirety.

TECHNICAL FIELD

The present invention relates to the field of biotechnology, more specifically, to primers for identifying serotypes of *Shigella flexneri* and to multiplex amplifications using the same.

BACKGROUND OF THE INVENTION

*Shigella* species are the major pathogenic bacteria causing bacterial diarrhea in developing countries, which infect 164.7 million people and lead to 0.11 million deaths per year, most of which are children under 5 years old (Kotloff, K. L., J. P. Winickoff, B. Ivanoff, J. D. Clemens, D. L. Swerdlow, P. J. Sansonetti, G. K. Adak, and M. M. Levine. 1999. Global burden of *Shigella* infections: implications for vaccine development and implementation of control strategies. Bull World Health Organ 77:651-66). Among the four serogroups of *Shigella, Shigella flexneri* is the predominant serogroup that affects the low-income population.

*Shigella flexneri* is further classified into various serotypes according to the different 0-antigen structures. To date, at least 15 serotypes have been reported, i.e. 1a, 1b, 1c, 2a, 2b, 3a, 3b, 4a, 4b, 5a, 5b, X, Xv, Y, and F6 (Simmons, D. A., and E. Romanowska. 1987. Structure and biology of *Shigella flexneri* O antigens. J. Med. Microbiol. 23:289-302; Stagg, R. M., S. S. Tang, N. I. Carlin, K. A. Talukder, P. D. Cam, and N. K. Verma. 2009. A novel glucosyltransferase involved in O-antigen modification of *Shigella flexneri* serotype 1c. J. Bacteriol. 191:6612-7; Ye, C., R. Lan, S. Xia, J. Zhang, Q. Sun, S. Zhang, H. Jing, L. Wang, Z. Li, Z. Zhou, A. Zhao, Z. Cui, J. Cao, D. Jin, L. Huang, Y. Wang, X. Luo, X. Bai, P. Wang, Q. Xu, and J. Xu. 2010. Emergence of a new multidrug-resistant serotype X variant in an epidemic clone of *Shigella flexneri*. J. Clin. Microbiol. 48:419-26). Serotyping has long been use to characterize isolates for epidemiological purposes The LPSs of all *Shigella flexneri* serotypes except F6 have the same polysaccharide backbone consisting of repeating tetrasaccharide units, and serotype Y has the basic tetrasaccharide backbone (Simmons, D. A., and E. Romanowska. 1987. Structure and biology of *Shigella flexneri* O antigens. J. Med. Microbiol. 23:289-302). Modification by glycosylation and/or acetylation of different sugars on the backbone gives rise to various type-specific antigenic determinants (e.g., I, II, III, IV, V, and VI), group-specific antigenic determinants (e.g., 3,4; 6; and 7,8), and antigenic determinant 1c (Stagg, R. M., S. S. Tang, N. I. Carlin, K. A. Talukder, P. D. Cam, and N. K. Verma. 2009. A novel glucosyltransferase involved in O-antigen modification of *Shigella flexneri* serotype 1c. J. Bacteriol. 191:6612-7).

Three genes (gtrA, gtrB, and gtr$_{[type]}$) are responsible for glycosylation modifications on *Shigella flexneri*. The first two genes are highly homologous and interchangeable, whereas the third gene gtr$_{[type]}$ is unique, and encodes serotype-specific glycosyltransferases (Allison, G. E., and N. K. Verma. 2000. Serotype-converting bacteriophages and O-antigen modification in *Shigella flexneri*. Trends. Microbiol. 8:17-23; Stagg, R. M., S. S. Tang, N. I. Carlin, K. A. Talukder, P. D. Cam, and N. K. Verma. 2009. A novel glucosyltransferase involved in O-antigen modification of *Shigella flexneri* serotype 1c. J. Bacteriol. 191:6612-7). Gtr genes specific to type-antigens I, II, IV and V, group antigen 7,8 and antigen 1c are gtrI, gtrII, gtrIV, gtrV, gtrX and gtrIC, respectively (Adams, M. M., G. E. Allison, and N. K. Verma. 2001. Type IV O antigen modification genes in the genome of *Shigella flexneri* NCTC 8296. Microbiology 147:851-60; Adhikari, P., G. Allison, B. Whittle, and N. K. Verma. 1999. Serotype 1a O-antigen modification: molecular characterization of the genes involved and their novel organization in the *Shigella flexneri* chromosome. J Bacteriol 181:4711-8; Guan, S., D. A. Bastin, and N. K. Verma. 1999. Functional analysis of the O antigen glucosylation gene cluster of *Shigella flexneri* bacteriophage SfX. Microbiology 145: 1263-73; Huan, P. T., D. A. Bastin, B. L. Whittle, A. A. Lindberg, and N. K. Verma. 1997. Molecular characterization of the genes involved in O-antigen modification, attachment, integration and excision in *Shigella flexneri* bacteriophage SfV. Gene 195:217-27; Mavris, M., P. A. Manning, and R. Morona. 1997. Mechanism of bacteriophage SfII-mediated serotype conversion in *Shigella flexneri*. Mol Microbiol 26:939-50; Stagg, R. M., S. S. Tang, N. I. Carlin, K. A. Talukder, P. D. Cam, and N. K. Verma. 2009. A novel glucosyltransferase involved in O-antigen modification of *Shigella flexneri* serotype 1c. J Bacteriol 191:6612-7). The gtr genes are carried by prophages integrated in the genome of host bacteria. O-acetylation, which confers group-antigen 6 and/or type-antigen III on strains of serotypes 1b, 3a, 3b and 4b, is mediated by the oac gene carried in bacteriophage Sf6 (Clark, C. A., J. Beltrame, and P. A. Manning. 1991. The oac gene encoding a lipopolysaccharide O-antigen acetylase maps adjacent to the integrase-encoding gene on the genome of *Shigella flexneri* bacteriophage Sf6. Gene 107:43-52; Verma, N. K., J. M. Brandt, D. J. Verma, and A. A. Lindberg. 1991. Molecular characterization of the O-acetyl transferase gene of converting bacteriophage Sf6 that adds group antigen 6 to *Shigella flexneri*. Mol. Microbiol. 5:71-5). Strains of different serotypes carry one or more serotype-specific prophages that encode different specific 0-antigen modifications genes (see FIG. 1).

Currently, the method for routinely identifying *Shigella flexneri* serotypes is the slide agglutination method using rabbit-originated antiserum raised against *Shigella flexneri*-specific type- and group-factors. Commercially available diagnostic sera have been widely used in microbiology laboratories. However, such a method has some disadvantages. Firstly, to identify the serotype of one *Shigella* strain, the slide agglutination method requires as many as 10 reaction tests, using antibodies against type-antigens I, II, III, IV, V and VI, antibodies against group-antigens 3,4 and 7,8, and the monoclonal antibody against serotype 1c (MASF1c), respectively (Stagg, R. M., P. D. Cam, and N. K. Verma. 2008. Identification of newly recognized serotype 1c as the most prevalent *Shigella flexneri* serotype in northern rural Vietnam. Epidemiol Infect 136:1134-40; Talukder, K. A., Z. Islam, M. A. Islam, D. K. Dutta, A. Safa, M. Ansaruzzaman, A. S. Faruque, S. N. Shahed, G. B. Nair, and D. A. Sack. 2003. Phenotypic and genotypic characterization of provisional serotype *Shigella flexneri* 1c and clonal relationships with 1a and 1b strains isolated in Bangladesh. J Clin Microbiol 41:110-7; Ye, C., R. Lan, S. Xia, J. Zhang, Q. Sun, S. Zhang, H. Jing, L. Wang, Z. Li, Z. Zhou, A. Zhao, Z. Cui, J. Cao, D. Jin, L. Huang, Y. Wang, X. Luo, X. Bai, P. Wang, Q. Xu, and J. Xu. 2010. Emergence of a new multidrug-resistant serotype X variant in an epidemic clone of *Shigella flexneri*. J Clin Microbiol 48:419-26). Secondly, visual assessment of the slide agglutination reactions may deliver incorrect readings. Thirdly, expensive antiserum kits limit the application of such a method in laboratories in developing countries.

Therefore, development of a rapid, specific identification method based on biomolecular technologies such as PCR will be significant for timely and accurate identification of *Shigella flexneri* serotypes.

SUMMARY OF THE INVENTION

One objective of the present invention is to provide a set of primers for identifying *Shigella flexneri* serotypes so as to identify *Shigella flexneri* serotypes by multiplex amplification, in acknowledgement of the O-antigen modification genes of *Shigella flexneri*.

Another objective of the present invention is to provide the use of the primers, in particular, for identification of *Shigella flexneri* serotypes and for preparation of agents for identifying *Shigella flexneri* serotypes.

Yet another objective of the present invention is to provide a method for identifying *Shigella flexneri* serotypes by multiplex amplification using the primers.

Still another objective of the present invention is to provide agents for identifying *Shigella flexneri* serotypes, such as a kit.

In one aspect of the present' invention, a set of primers for multiplex amplification used for identification of *Shigella flexneri* serotypes is designed based on genes gtrI, gtrII, oac, gtrIV, gtrV, gtrX, $wzx_{1-5}$ and gtrIC. The set of primers includes amplification primers for identifying target genes gtrI, gtrII, oac, gtrIV, gtrV, gtrX, $wzx_{1-5}$ and gtrIC. In a particular embodiment of the present invention, amplification primers having specificity and a common annealing temperature are designed based on known sequences of genes gtrI, gtrII, oac, gtrIV, gtrV, gtrX, $wzx_{1-5}$ and gtrIC, and more specifically, are the following amplification primers of the present invention: SEQ ID Nos. 1 and 2, for amplification of the gtrI gene fragment; SEQ ID Nos. 3 and 4, for amplification of the gtrII gene fragment; SEQ ID Nos. 5 and 6, for amplification of the oac gene fragment; SEQ ID Nos. 7 and 8, for amplification of the gtrIV gene fragment; SEQ ID Nos. 9 and 10, for amplification of the gtrV gene fragment; SEQ ID Nos. 11 and 12, for amplification of the gtrX gene fragment; SEQ ID Nos. 13 and 14, for amplification of the $wzx_{1-5}$ gene fragment; and SEQ ID Nos. 15 and 16, for amplification of the gtrIC gene fragment.

The primers of the invention can be used for qualitative identification of *Shigella flexneri* serotypes. All currently known serotypes can be successfully identified, except for serotype Xv, which cannot be distinguished from serotype X.

According to a preferred embodiment of the present invention, the set of primers for identifying *Shigella flexneri* serotypes provided by the present invention may further include a primer pair specific to F6. The average isolation rate of serotype F6 in Asia is 6%, ranging from 0% (China) to 15% (Pakistan) (von Seidlein, L., D. R. Kim, M. Ali, H. Lee, X. Wang, V. D. Thiem, G. Canh do, W. Chaicumpa, M. D. Agtini, A. Hossain, Z. A. Bhutta, C. Mason, O. Sethabutr, K. Talukder, G. B. Nair, J. L. Deen, K. Kotloff, and J. Clemens. 2006. A multicentre study of *Shigella* diarrhoea in six Asian countries: disease burden, clinical manifestations, and microbiology. PLoS Med 3:e353). It is necessary to introduce an F6-specific singleplex PCR for countries where F6 is prevalent. However, since the multiplex amplification primers of the present invention already contain 8 pairs of primers, adding an additional pair of primers increases the difficulty in optimizing the multiplex PCR. Thus, one has to be cautious when interpreting the amplification-negative strains in the multiplex PCR as serotype F6. According to a preferred embodiment of the present invention, a singleplex PCR is employed to confirm F6, and the primer pair for identifying F6 is SEQ ID Nos. 17 and 18 for amplification of the $wzx_6$ gene fragment. Furthermore, as the strains have been verified with polyvalent antisera for *Shigella* and serogroup B prior to the multiplex PCR, the probability of false-positive F6 is low.

In another aspect, the present invention further provides the use of the primers, particularly including the use of the primers for identification of *Shigella flexneri* serotypes and the use of the primers for preparation of agents for identifying *Shigella flexneri* serotypes.

Based on the use of the primers for identifying *Shigella flexneri* serotypes provided by the present invention, the present invention also establishes a set of rapid and sensitive methods ready for high-throughput application, for identifying *Shigella flexneri* serotypes by amplification. In particular, the method is a multiplex amplification identification method, comprising carrying out identification by multiplex amplification using the primers of the present invention, wherein the amplification is preferably polymerase chain reaction (PCR). Since the multiplex amplification technique involves multiple pairs of primers and multiple pairs of templates as compared with conventional amplification techniques, it is influenced by more factors and thus has a higher chance to give mismatched amplification products. Therefore, the design of the primers is crucial. In the present invention, on the basis of the designed multiple pairs of primers, the reaction system and conditions, especially the annealing temperature, are preferably optimized. In PCR, the PCR system is composed of heat-resistant DNA polymerases, primers, deoxynucleotides, DNA templates to be amplified, and a buffer. The present invention provides a preferred PCR reaction which is performed under the following conditions: pre-denaturation at 95° C. for 15 min; 30 cycles of: denaturation at 94° C. for 30 s, annealing at 55° C. for 90 s, and extension at 72° C. for 60 s; and final extension at 72° C. for 10 min.

The multiplex amplification-based identification method of the present invention preferably further includes performing a qualitative analysis after the amplification. The method for the qualitative analysis may be those known to a person skilled in the art, e.g., a method including visualization of amplification products using gel electrophoresis, in which case a person skilled in the art can determine the gel and gel concentrations to be used, according to the sizes of the amplification products.

In order to validate the effectiveness of the method of the present invention, in particular embodiments of the present invention, the primers of the present invention were used to conduct amplification on strains representing 14 currently common *Shigella flexneri* serotypes by multiplex PCR, and 358 *Shigella flexneri* strains of various serotypes were analyzed. The multiplex PCR results for the assayed strains have a concordance of 97.8% with those obtained by the slide agglutination method. In order to assess the specificity of the primers of the present invention, 50 non flexneri strains, including other *Shigella* serogroups and enteric pathogens, were also examined in particular embodiments of the present invention. These bacteria were all negative in the amplification, proving that the specificity of the method of the present invention is 100%. These results demonstrate that timely and accurate identification of *Shigella flexneri* serotypes can be achieved by using the primers and the amplification-based identification method of the present invention.

According to the use of the primers in the preparation of agents for identifying *Shigella* serotypes as provided in the present invention, the identification agents of the present invention are preferably used to assay isolated *Shigella flexneri* strains. According to particular embodiments of the present invention, the identification agents may be a kit. The identification agents may be used to assay *Shigella flexneri* or assay *Shigella flexneri*-containing samples used for identification and diagnosis. In the present invention, the identification agents are preferably used to assay excrement, intestinal effusions, and vomit. The multiplex amplification primers and the multiplex amplification method of the present invention are highly specific, can be used alone as a rapid identification method to assay enriched or unenriched samples, such as ex vivo samples from patients (for example, excrement, effusions, vomit, etc.) and water, soil, food, and cosmetics that may carry *Shigella flexneri*, and can achieve rapid diagnosis and identification of *Shigella flexneri* serotypes.

The present invention further provides a kit for identifying *Shigella flexneri* serotypes, which contains the primers of the present invention. The kit may further comprise target-detecting probes for detecting target genes, and the probes are for example SEQ ID No.19, SEQ ID No.20, SEQ ID No.21, SEQ ID No.22, SEQ ID No.23, SEQ ID No.24, SEQ ID No.25 and SEQ ID No.26. The kit of the present invention can be used to qualitatively identify *Shigella flexneri* serotypes.

Among *Shigella flexneri*, serotypes X and Xv have the same amplification pattern ($wzx_{1-5}$ and gtrX). Thus, they are classified as the same serotype Xv or X by the multiplex PCR method. Serotype Xv has been one of the most prevalent serotypes in China since 2002 (Ye, C., R. Lan, S. Xia, J. Zhang, Q. Sun, S. Zhang, H. Jing, L. Wang, Z. Li, Z. Zhou, A. Zhao, Z. Cui, J. Cao, D. Jin, L. Huang, Y. Wang, X. Luo, X. Bai, P. Wang, Q. Xu, and J. Xu. 2010. Emergence of a new multidrug-resistant serotype X variant in an epidemic clone of *Shigella flexneri*. J Clin Microbiol 48:419-26), which was initially designated as 4c as it can react with both anti-type IV sera and anti-group 7,8 sera (Pryamukhina, N. S., and N. A. Khomenko. 1988. Suggestion to supplement *Shigella flexneri* classification scheme with the subserovar *Shigella flexneri* 4c: phenotypic characteristics of strains. J Clin Microbiol 26:1147-9). However, since factors responsible for type IV antigenic determinant have not been clarified (Ye, C., R. Lan, S. Xia, J. Zhang, Q. Sun, S. Zhang, H. Jing, L. Wang, Z. Li, Z. Zhou, A. Zhao, Z. Cui, J. Cao, D. Jin, L. Huang, Y. Wang, X. Luo, X. Bai, P. Wang, Q. Xu, and J. Xu. 2010. Emergence of a new multidrug-resistant serotype X variant in an epidemic clone of *Shigella flexneri*. J Clin Microbiol 48:419-26), it is currently impossible to develop a PCR method to identify serotype Xv. In order to differentiate between serotypes Xv and X, an additional slide agglutination reaction using anti-type IV serum would be necessary.

Above all, according to the present invention, specific primers with a common annealing temperature used for identifying *Shigella flexneri* serotypes have been designed, and a multiplex PCR identification method based on the genes of *Shigella flexneri* O antigen-modification enzymes has been established. The multiplex PCR method of the present invention may be employed for biomolecular identification of *Shigella flexneri* serotypes, and the majority of currently known serotypes (14 out of 15) can be easily and specifically identified in only one reaction. In comparison with the conventional slide agglutination method (requiring as many as 10 independent reactions), the multiplex PCR method of the present invention is time-saving, does not require expensive antisera, and is especially suitable for high-throughput identification. With this method, identification of 96 samples can be completed within 3.5 hours and costs only 25% of that of the slide method. The amplification primers and the multiplex amplification method of the present invention may be used to complement the serum agglutination method for identification of *Shigella flexneri* serotypes, and are practically significant and highly valuable for timely and accurate identification of serotypes of clinical isolates of pathogenic bacteria and for prevention and treatment of shigellosis.

DESCRIPTION OF THE DRAWINGS

FIG. 1 shows the chemical composition and genes responsible for specific modifications of the O antigens of various *Shigella flexneri* serotypes.

FIG. 2 shows the multiplex PCR amplification results of reference strains of 14 serotypes. The results were obtained by using the method of the present invention, wherein M1 and M2 are 150 bp and 100 bp DNA Ladder Markers (purchased from TaKaRa, Japan), respectively.

FIG. 3 shows the specificity assay results of 50 non-*Shigella flexneri* strains. In the results, M: marker; C: positive control; 1-2: *Shigella sonnei*, phases I, II; 3-14: *Shigella dysenteriae* serotypes 1-12; 15-32: *Shigella boydii* serotypes 1-18; 33-34: Enteroaggregative *E. coli;* 35-37: Enterohemorrhagic *E. coli* 0157:H7; 38: Enteroinvasive *E. coli;* 39: Enteropathogenic *E. coli;* 40: Enterotoxigenic *E. coli;* 41: Uropathogenic *E. coli;* 42-43: *E. coli* K12; 44: *L monocytogenes;* 45: *V. cholera;* 46: *Salmonella paratyphi* A; 47-48: *Salmonella paratyphi* B; 49: *Yersinia enterocolitica;* 50: *Salmonella choleraesuis.*

DETAILED DESCRIPTION

The present invention will be further described with reference to the following examples and the figures, for better understanding of the invention. The examples are only illustrative and are not in any way limiting the scope of the present invention. In the examples, any experimental methods without detailed conditions specified are conventional methods with conventional conditions well known in the art or conditions recommended by the manufacturer.

EXAMPLES

Materials and Methods

Strains: 14 known *Shigella flexneri* serotypes (except serotype 5b, see Table 1 for details) were used in the examples to establish the conditions for performing the multiplex PCR method. 358 *Shigella flexneri* strains in total (Table 2) were used to evaluate the effectiveness of the multiplex PCR method of the present invention. In order to examine the cross-reactions of the primers in this study, 50 strains from different genera were examined (*S. Sonnei* (n=2), *S. dysenteriae* (n=12, including all 12 serotypes), *S. boydii* (n=18, including all 18 serotypes), Enteroaggregative

*E. coli* (n=2), Enterohemorrhagic *E. coli* O 157:H7 (n=3), Enteroinvasive *E. coli* (n=1), Enteropathogenic *E. coli* (n=1), Enterotoxigenic *E. coli* (n=1), Uropathogenic *E. coli* (n=1), *E. coli* K12 (n=2), *L. monocytogenes* (n=1), *V. cholera* (n=1), *Salmonella paratyphi* A (n=1), *Salmonella paratyphi* B (n=2), *Yersinia enterocolitica* (n=1), and *Salmonella choleraesuis* (n=1)). The serotypes of all the *Shigella flexneri* strains were confirmed with polyvalent antisera (purchased from Denka Seiken, Japan) and monoclonal antibodies (purchased from Reagensia AB, Sweden). All Chinese strains used in the examples were isolated from diarrhea patients in Chinese and were preserved in the Microbiology Laboratory, National Institute for Communicable Disease Control and Prevention, Chinese Center for Disease Control and Prevention (China CDC). Other strains were purchased from National Collection of Type Cultures (NCTC), UK.

Preparation of DNA Templates

DNA templates were directly obtained from bacteria clones by the boiling method. A single colony from an overnight culture on an LB plate was firstly put into 30 μl distilled water, boiled at 100° C. for 10 min, placed into an ice bath for 5 min, and centrifuged at 13,000×g, 4° C. for 10 min. The supernatant was used as the templates for PCR amplification.

PCR Primers

The PCR primers used in the examples are listed in Table 3, the primers for amplification of the wzx gene were designed with reference to Yayue Li et al. (Li, Y., B. Cao, B. Liu, D. Liu, Q. Gao, X. Peng, J. Wu, D. A. Bastin, L. Feng, and L. Wang. 2009. Molecular detection of all 34 distinct O-antigen forms of *Shigella*. J Med Microbiol 58:69-81), and other primers were designed according to the sequences of *Shigella flexneri* serotype-specific genes gtrI, gtrIC, gtrII, oac, gtrIV, gtrV, and gtrX.

All primers were synthesized by Sangon Biotech (Shanghai) as commissioned, and dissolved in TL buffer (10 mM Tris-Cl, 1 mM EDTA, pH 8.0) to have a final concentration of 50 μM.

PCR Amplification and Identification

Multiplex PCRs were carried out using a QIAGEN Multiplex PCR Kit (QIAGEN). Each PCR reaction mixture comprises 1×PCR Master Mix (containing HotStarTaq DNA polymerase, Multiplex PCR buffer, and dNTP Mix), primers (0.2 μM each) and 3 μl DNA templates, and is 50 μl in total. In the examples, PCR amplification was performed based on the PCR conditions provided by the kit instructions in which some multiplex PCR cycling parameters were further optimized, Le, pre-denaturation at 95° C. for 15 min; totally 30 cycles of denaturation at 94° C. for 30s, annealing at 55° C. for 90 s, extension at 72° C. for 60 s; and final extension at 72° C. for 10 min. The amplification was performed in a thermocycler from SENSO (Germany). 5 microliter of amplification products was mixed with loading buffer, electrophoresed on a 1.5% agarose gel, and visualized using EB staining for results. Where necessary, the PCR products were directly sequenced or cloned into a pMD20-T TA cloning vector (TaKaRa, Japan) for cloning and sequencing.

Experimental Results

Figure 2:
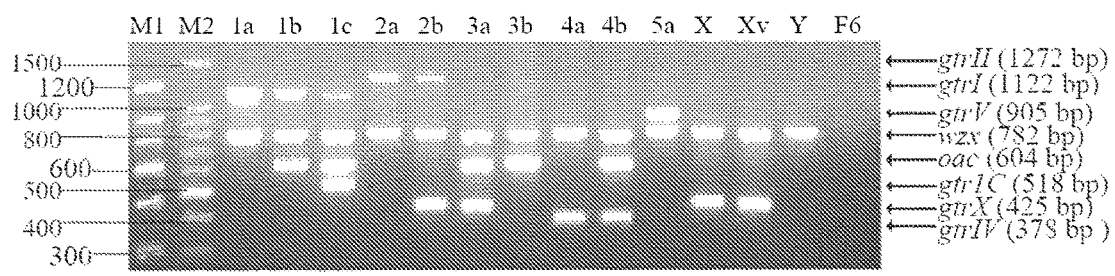

In the examples, reference strains were firstly subjected to singleplex PCR with the primers, and as a results, every pair of primers can give the expected fragments after amplification, namely 783 bp ($wzx_{1-5}$), 1122 bp (gtrI), 518 bp (gtrIC), 1268 bp (gtrII), 604 bp (oac), 378 bp (gtrIV), 905 bp (gtrV) and 425 bp (gtrX), respectively. Sequencing of the PCR amplification products proved that the amplified fragments were correct. Afterwards, multiplex PCR was carried out according to the protocols described above in Materials and Methods, in which we tried different annealing temperatures from 54° C. to 63° C. and found that the highest yield was obtained at 55° C. The results showed that different serotypes have different amplification patterns (see FIG. 2 and Table 1). The expected specific PCR products were obtained from the amplification of each serotype. The amplified fragments of different sizes can be well resolved on a 1.5% gel, and with two different DNA markers, each PCR product can be correctly identified by size. The amplification patterns of the reference strains are as follows: 1a ($wzx_{1-5}$, gtrI), 1b ($wzx_{1-5}$, gtrI, oac), 1c ($wzx_{1-5}$, gtrI, gtrIC), 2a ($wzx_{1-5}$, gtrII), 2b ($wzx_{1-5}$, gtrII, gtrX), 3a ($wzx_{1-5}$, oac, gtrX), 3b ($wzx_{1-5}$, oac), 4a ($wzx_{1-5}$, gtrIV), 4b ($wzx_{1-5}$, gtrIV, oac), 5a ($wzx_{1-5}$, gtrV), X/Xv ($wzx_{1-5}$, gtrX) and Y ($wzx_{1-5}$). $wzx_{1-5}$ may also be used as a reference gene for PCR reactions since it is present in all *Shigella flexneri* serotypes except serotype F6, F6 is negative in the amplification as its O-antigen synthesizing genes are completely different from those of other serotypes, and does not have any genes for modifications (Cheah, K. C., D. W. Beger, and P. A. Manning. 1991. Molecular cloning and genetic analysis of the rfb region from *Shigella flexneri* type 6 in *Escherichia coli* K-12. FEMS Microbiol Lett 67:213-8; Simmons, D. A., and E. Romanowska., 1987. Structure and biology of *Shigella flexneri* O antigens. J Med Microbiol 23:289-302).

In the examples, we attempted to incorporate a pair of specific primers for F6 in the reaction. However, the additional pair of primers increases the difficulty in optimization of the multiplex PCR since the reaction already contains 8 pairs of primers. Hence, no good results were obtained after experimentation with 3 pairs of such primers (designed according to the sequence of F6-specific O-antigen gene $wzx_6$), and one should be cautious when interpreting a strain negative in the amplification as serotype F6. According to preferred embodiments of the present invention, a singleplex PCR was used to confirm F6, the primers for which can be seen in Table 3, and the length of the amplified product is 739 bp. Furthermore, since all strains have been verified with polyvalent antisera for *Shigella* and serogroup B, possibility of a false-positive F6 is very low.

It is noteworthy that the primers for amplification of the oac gene were designed based on the conserved regions in oac and $oac_{1b}$ (which share 88% identity) to guarantee both can be amplified. Although a serotype 5b strain was not available, it can be predicted that the amplification pattern of serotype 5b is 905 bp (gtrV) and 425 bp (gtrX) according to the O antigen-modification characteristics of this serotype. As there are not any typical strains of serotype 1c, a serotype F1 strain (untypable), 06HN081 (this strain can react with the 1c-specific monoclonal antibody MASF1c), was used in the present invention to detect the serotype 1c-specific gene gtrIC. As compared to typical 1c strains (which react exclusively with MASF1c), this F1 strain (untypable) can react with both MASF1c and group 6 antisera. Accordingly, the genes gtrIC and oac that encode the antigen of MASF1c and the group 6 antigen were both identified as positive. These results indicate that this F1 (untypable) strain is converted from serotype 1b having its O-antigen modified by GtrIC, and is therefore a new serotype (see Table 1). This new serotype has the same serological reaction pattern as the strain of serotype 7b reported in Forster et al., and thus the serotype of 06HN081 should be 7b. It is to be noted that 1c is designated in Forster et al. as 7a (Foster, R. A., N. I. Carlin, M. Majcher, H. Tabor, L. K. Ng, and G. Widmalm. Structural elucidation of the O-antigen of the *Shigella flexneri* provisional serotype 88-893: structural and serological similarities with *S. flexneri* provisional serotype Y394 (1c). Carbohydr Res 346:872-6). Hence, these two new serotypes can be identified by the multiplex PCR of the present invention. The present invention further provides the use of the primers, the multiplex PCR method, and the kit for identifying these two new serotypes.

Serotypes X and Xv have the same amplification pattern ($wzx_{1-5}$ and gtrX). Thus, they are classified as the same serotype Xv/X by the multiplex PCR method.

Figure 3:
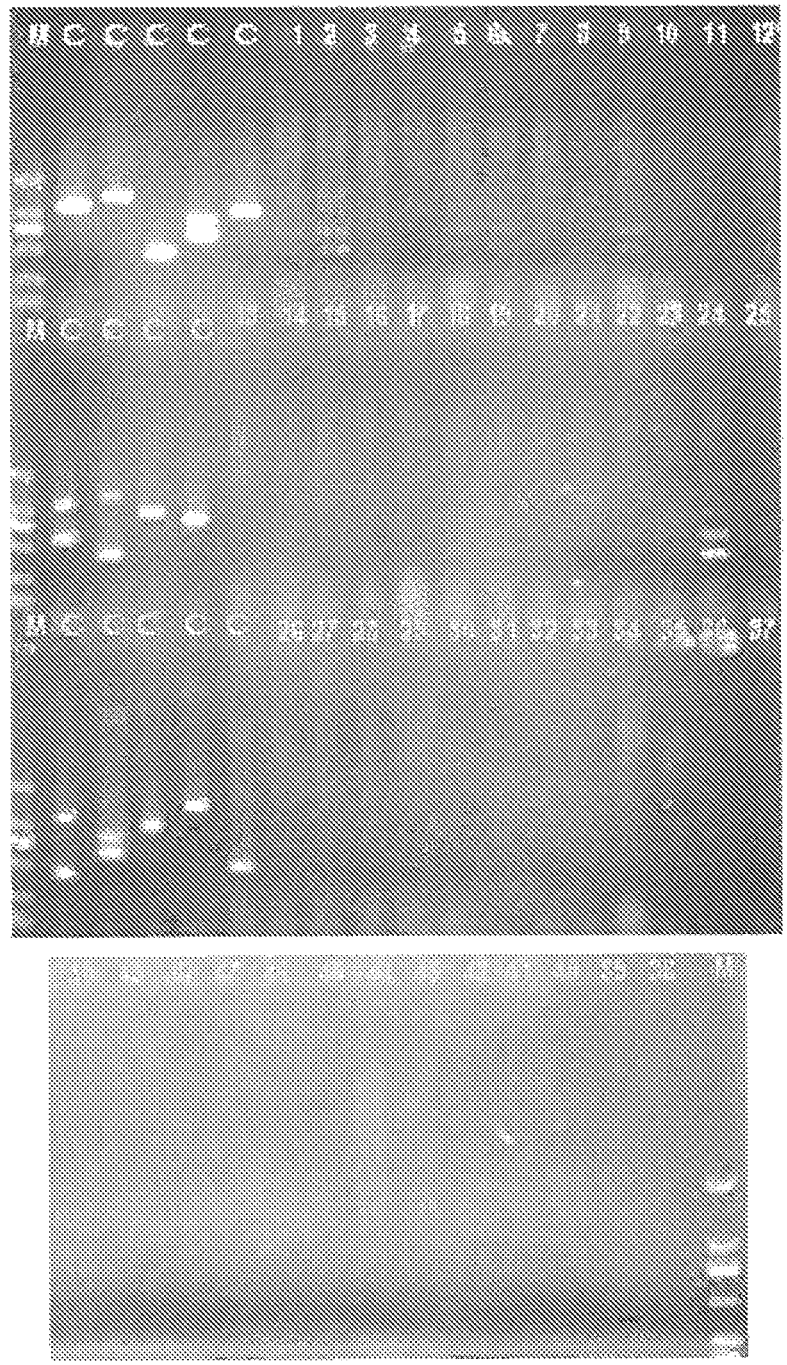

In order to evaluate the specificity of the primers, 50 non-*Shigella flexneri* strains were tested in the examples, including other *Shigella* serogroups and enteric pathogens. These bacteria all showed negative after the amplification (see FIG. 3), indicating the specificity of the method of the present invention is 100%.

To determine whether the method of the present invention is applicable to all *Shigella flexneri* strains, and to assess the effectiveness of the method of the present invention, 358 *Shigella flexneri* strains of various serotypes were analyzed in the examples (see Table 2). The multiplex PCR results of nearly all tested strains (except 8 strains) are consistent with the slide agglutination results, with a concordance rate of 97.8%.

TABLE 1

Serotype characteristics of *S. flexneri* reference strains by agglutination and multiplex PCR

| | | Serum Agglutination Reaction | | | | | | | | | Multiplex PCR | | | | | | | |
|---|---|---|---|---|---|---|---|---|---|---|---|---|---|---|---|---|---|---|
| | | Type Antigen | | | | | | Group Antigen | | MASF | | | | | | | | |
| Strain No. | Serotype | I | II | III | IV | V | VI | 3,4 | 6 | 7,8 | 1c | wzx | gtrI | gtrIC | gtrII | oac | gtrIV | gtrV | gtrX |
| 2000019 | 1a | + | − | − | − | − | − | + | − | − | − | + | + | − | − | − | − | − | − |
| 1997020 | 1b | + | − | − | − | − | − | + | + | − | − | + | + | − | − | + | − | − | − |
| 06HN081# | — | − | − | − | − | − | − | − | + | − | + | + | + | + | − | + | − | − | − |
| 301 | 2a | − | + | − | − | − | − | + | − | − | − | + | − | − | + | − | − | − | − |
| NCTC4 | 2b | − | + | − | − | − | − | − | − | + | − | + | − | − | + | − | − | − | + |
| 03HL12 | 3a | − | − | + | − | − | − | − | + | + | − | + | − | − | − | + | − | − | + |
| 2002110 | 3b | − | − | + | − | − | − | − | + | − | − | + | − | − | − | + | − | − | − |
| NCTC9725 | 4a | − | − | − | + | − | − | + | − | − | − | + | − | − | − | − | + | − | − |
| NCTC9726 | 4b | − | − | − | + | − | − | − | + | − | − | + | − | − | − | + | + | − | − |
| 51247 | 5a | − | − | − | − | + | − | + | − | − | − | + | − | − | − | − | − | + | − |
| 2003036 | Y | − | − | − | − | − | − | + | − | − | − | + | − | − | − | − | − | − | − |
| 2001014 | X | − | − | − | − | − | − | − | − | + | − | + | − | − | − | − | − | − | + |
| 2002017 | Xv | − | − | − | + | − | − | − | − | + | − | + | − | − | − | − | − | − | + |
| 2000007 | F6 | − | − | − | − | − | + | − | − | − | − | − | − | − | − | − | − | − | − |

Atypical F1 type, positive for both MASF1c and group 6 antiserum

TABLE 2

Correlation between the test results obtained from the multiplex PCR method and the slide agglutination method for 358 *Shigella flexneri* strains of various serotypes.

| Serotype | No. of Strains | Target Gene | | | | | | | | Multiplex PCR serotype classification |
|---|---|---|---|---|---|---|---|---|---|---|
| | | $wzx_{1-5}$ | gtrI | gtrIC | gtrII | oac | gtrIV | gtrV | gtrX | |
| F1a | 25 | 25 | 25 | 0 | 0 | 0 | 0 | 0 | 0 | 1a (25) |
| F1b | 14 | 14 | 14 | 0 | 0 | 14 | 0 | 0 | 0 | 1b (14) |
| F2a | 55 | 55 | 0 | 0 | 55 | 0 | 0 | 0 | 0 | 2a (55) |
| F2b | 50 | 50 | 0 | 0 | 50 | 0 | 0 | 0 | 50 | 2b (50) |
| F3a | 10 | 10 | 0 | 0 | 0 | 10 | 0 | 0 | 10 | 3a (10) |
| F3b | 2 | 2 | 0 | 0 | 0 | 2 | 0 | 0 | 0 | 3b (2) |
| F4a | 5 | 5 | 0 | 0 | 0 | 0 | 5 | 0 | 0 | 4a (5) |
| F4b | 5 | 5 | 0 | 0 | 0 | 5 | 5 | 0 | 0 | 4b (5) |
| F5a | 4 | 4 | 0 | 0 | 0 | 1 | 0 | 4 | 0 | 5a (3), untypable (1) |
| Y | 36 | 36 | 0 | 0 | 5 | 0 | 0 | 0 | 0 | Y (31), 2a (5) |
| Xv | 78 | 78 | 0 | 0 | 0 | 0 | 0 | 0 | 78 | X or Xv (78) |
| X | 69 | 69 | 0 | 0 | 2 | 0 | 0 | 0 | 69 | X or Xv (67), 2b (2) |
| F6 | 5 | 0 | 0 | 0 | 0 | 0 | 0 | 0 | 0 | F6 |

TABLE 3

Primers Used in the Examples

| Target Gene | Primer sequence (5'→3') | Length of Amplified Fragments (bp) | Serotype Specificity | Accession no. |
|---|---|---|---|---|
| gtrI | (F) CTGTTAGGTGATGATGGCTTAG (SEQ ID No. 1)<br>(R) ATTGAACGCCTCCTTGCTATGC (SEQ ID No. 2) | 1122 (SEQ ID No. 19) | 1a, 1b, 1c | AF139596 |
| gtrII | (F) ATTTATTGTTATTGGGGGTGGTTG (SEQ ID No. 3)<br>(R) ATTTGTTCTTTATTTGCTGGTT (SEQ ID No. 4) | 1268 (SEQ ID No. 20) | 2a, 2b | AF021347 |
| oac | (F) CTGTTCGGCTTTGAAAGTGCTG (SEQ ID No. 5)<br>(R) CGTAGGCGTACATAGCAAGCAAAGA (SEQ ID No. 6) | 604 (SEQ ID No. 21) | 1b, 3a, 3b, 4b | AF547987 |
| gtrIV | (F) ATGTTCCTCCTTCTTCCTTT (SEQ ID No. 7)<br>(R) TCCTGATGCTACCTTATCCA (SEQ ID No. 8) | 378 (SEQ ID No. 22) | 4a, 4b | AF288197 |
| gtrV | (F) AATACGATTCTCCTGGTGCTAAAC (SEQ ID No. 9)<br>(R) TAGGGCATTGCTTGTATCTTTCAT (SEQ ID No. 10) | 905 (SEQ ID No. 23) | 5a, 5b | U82619 |
| gtrX | (F) AATGCTGGATGGGATAATCACCTT (SEQ ID No. 11)<br>(R) GAGACGGCTTCTCCATGTTTTGCT (SEQ ID No. 12) | 425 (SEQ ID No. 24) | 2b, 3a, 5b, X, Xv | L05001 |
| $wzx_{1-5}$ | (F) CACTTGTTGGGTATGCTGG (SEQ ID No. 13)<br>(R) CCGGCAAACAGATTAGAAA (SEQ ID No. 14) | 783 (SEQ ID No. 25) | 1-5, X, Xv, Y | AE005674 |
| gtrIC | (F) AGGGAATGGCATTAGGGATCGG (SEQ ID No. 15)<br>(R) GCTGCAAGTGGTTTTTGTTGGA (SEQ ID No. 16) | 518 (SEQ ID No. 26) | 1c | FJ905303 |
| $wzx_6^S$ | (F) TTAAGAGCGATCATTTC (SEQ ID No. 17)<br>(R) CCATCCAAGCGGACATT (SEQ ID No. 18) | 739 (SEQ ID No. 27) | F6 | EU294165 |

$^S$The primer pair for $wzx_6$ is used to conform serotype F6.

The multiplex PCR method of the present invention may be employed to conduct biomolecular identification of *Shigella flexneri* serotypes in only one reaction, and can easily and specifically identify the majority of currently known serotypes (14 out of 15). In comparison with the conventional slide agglutination method (which requires as many as 10 independent reactions), the multiplex PCR method of the present invention is time-saving, does not require expensive antisera, and is especially suitable for high-throughput identification. Using this method, identification of 96 samples can be completed within 3.5 hours and costs only 25% of that of the slide agglutination method.

The invention claimed is:

1. A method for identifying *Shigella flexneri* serotypes, comprising performing amplification on a sample using a set of primers comprising the following primer pair nucleic acid sequences: SEQ ID NOs:1 and 2, SEQ ID NOs: 3 and 4, SEQ ID NOs: 5 and 6, SEQ ID NOs: 7 and 8, SEQ ID NOs: 9 and 10, SEQ ID NOs: 11 and 12, SEQ ID NOs: 13 and 14, and SEQ ID NOs: 15 and 16.

2. The method according to claim 1, wherein the set of primers comprises the primer pair nucleic acid sequences of SEQ ID NOs: 17 and 18.

3. The method according to claim 1, wherein the amplification is a polymerase chain reaction.

4. The method according to claim 3, wherein the polymerase chain reaction is a multiplex polymerase chain reaction.

5. The method according to claim 4, further comprising performing singleplex PCR amplification on a sample using a pair of primers comprising the nucleic acid sequences of SEQ ID NOs: 17 and 18.

6. The method according to claim 1, further comprising performing a qualitative analysis after the amplification.

7. The method according to claim 6, wherein the qualitative analysis comprises visualization of the amplified products through gel electrophoresis.

8. The method according to claim 1, further comprising conducting a slide agglutination reaction using anti-group IV antisera to further differentiate between serotypes Xv and X.

9. The method according to claim 1, wherein the sample is obtained from an isolated *Shigella flexneri* strain.

10. The method according to claim 1, wherein the sample is an enriched or unenriched sample selected from the group consisting of: an excrement sample, an intestinal effusion sample, and a vomit sample.

11. The method according to claim 1, wherein the sample is an enriched or unenriched sample selected from the group consisting of: a water sample, a soil sample, a food sample, and a cosmetic sample.

12. The method according to claim 1, wherein *Shigella flexneri* serotype 7a or 7b is identified by the amplification step.

* * * * *